(12) United States Patent
Heil et al.

(10) Patent No.: US 7,349,742 B2
(45) Date of Patent: Mar. 25, 2008

(54) EXPANDABLE FIXATION ELEMENTS FOR SUBCUTANEOUS ELECTRODES

(75) Inventors: Ron Heil, Roseville, MN (US); Darrell Orvin Wagner, Isanti, MN (US); Adam W. Cates, Minneapolis, MN (US); Curtis Charles Lindstrom, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/745,341

(22) Filed: Dec. 23, 2003

(65) Prior Publication Data
US 2004/0230281 A1    Nov. 18, 2004

Related U.S. Application Data

(60) Provisional application No. 60/462,272, filed on Apr. 11, 2003.

(51) Int. Cl.
*A61N 1/05* (2006.01)
(52) U.S. Cl. ..................................... 607/116
(58) Field of Classification Search ........ 607/115–130; 606/41, 108; 604/104; 600/116–126
See application file for complete search history.

(56) References Cited

U.S. PATENT DOCUMENTS

| | | | |
|---|---|---|---|
| 3,902,501 A | 9/1975 | Citron et al. | |
| 4,301,815 A | 11/1981 | Doring | |
| 4,562,841 A | 1/1986 | Brockway et al. | |
| 4,716,888 A | 1/1988 | Wesner | |
| 4,953,551 A | 9/1990 | Mehra et al. | |
| 5,036,849 A | 8/1991 | Hauck et al. | |
| 5,133,353 A | 7/1992 | Hauser | |
| 5,170,784 A | 12/1992 | Ramon et al. | |

(Continued)

FOREIGN PATENT DOCUMENTS

EP    0 517 494 A    9/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Scott M. Getzow
(74) *Attorney, Agent, or Firm*—Hollingsworth & Funk, LLC

(57) ABSTRACT

Subcutaneous systems and leads may be fixed in tissue after placement by use of one or more expanding fixation elements. An expanding fixation element is provided on an implantable lead and configured to secure one or both of a subcutaneous electrode and the lead body within subcutaneous non-intrathoracic tissue. A delivery apparatus comprising a sheath may be included that is configured to introduce the lead to a desired subcutaneous non-intrathoracic location within the patient. A method of lead delivery typically involves introducing a sheath into a subcutaneous non-intrathoracic body location of a patient, providing a lead comprising a lead body and an electrode, and advancing the lead through the sheath and to the subcutaneous non-intrathoracic body location. The method further involves fixing the lead to subcutaneous non-intrathoracic tissue using an expanding fixation element and thereafter removing the sheath from the patient.

51 Claims, 18 Drawing Sheets

U.S. PATENT DOCUMENTS

| | | | |
|---|---|---|---|
| 5,179,945 A | 1/1993 | Van Hofwegen et al. | |
| 5,203,348 A | 4/1993 | Dahl et al. | |
| 5,209,229 A | 5/1993 | Gilli | |
| 5,230,337 A | 7/1993 | Dahl et al. | |
| 5,261,400 A | 11/1993 | Bardy | |
| 5,284,136 A | 2/1994 | Hauck et al. | |
| 5,292,338 A | 3/1994 | Bardy | |
| 5,300,106 A | 4/1994 | Dahl et al. | |
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |
| 5,331,966 A | 7/1994 | Bennett et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,376,106 A | 12/1994 | Stahmann et al. | |
| 5,378,239 A * | 1/1995 | Termin et al. | 604/104 |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,468,254 A | 11/1995 | Hahn et al. | |
| 5,507,751 A * | 4/1996 | Goode et al. | 606/108 |
| 5,531,779 A | 7/1996 | Dahl et al. | |
| 5,545,202 A | 8/1996 | Dahl et al. | |
| 5,603,732 A | 2/1997 | Dahl et al. | |
| 5,620,466 A | 4/1997 | Haefner et al. | |
| 5,634,938 A | 6/1997 | Swanson et al. | |
| 5,641,326 A | 6/1997 | Adams | |
| 5,662,688 A | 9/1997 | Haefner et al. | |
| 5,697,953 A | 12/1997 | Kroll et al. | |
| 5,704,365 A | 1/1998 | Albrecht et al. | |
| 5,724,984 A | 3/1998 | Arnold et al. | |
| 5,827,326 A | 10/1998 | Kroll et al. | |
| 5,895,414 A | 4/1999 | Sanchez-Zambrano | |
| 5,902,329 A * | 5/1999 | Hoffmann et al. | 607/121 |
| 5,916,243 A | 6/1999 | KenKnight et al. | |
| 5,951,597 A * | 9/1999 | Westlund et al. | 607/126 |
| 5,957,956 A | 9/1999 | Kroll et al. | |
| 6,044,298 A | 3/2000 | Salo et al. | |
| 6,055,454 A | 4/2000 | Heemels | |
| 6,136,021 A | 10/2000 | Chastain et al. | |
| 6,148,230 A | 11/2000 | KenKnight | |
| 6,221,011 B1 | 4/2001 | Bardy | |
| 6,227,072 B1 | 5/2001 | Ritchey et al. | |
| 6,270,457 B1 | 8/2001 | Bardy | |
| 6,280,380 B1 | 8/2001 | Bardy | |
| 6,280,462 B1 | 8/2001 | Hauser et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,409,675 B1 | 6/2002 | Turcott | |
| 6,415,174 B1 | 7/2002 | Bebehani et al. | |
| 6,438,410 B2 | 8/2002 | Hsu et al. | |
| 6,440,066 B1 | 8/2002 | Bardy | |
| 6,480,733 B1 | 11/2002 | Turcott | |
| 6,491,639 B1 | 12/2002 | Turcott | |
| 6,512,940 B1 | 1/2003 | Brabec et al. | |
| 6,522,915 B1 | 2/2003 | Ceballos et al. | |
| 6,564,106 B2 | 5/2003 | Guck et al. | |
| 6,592,581 B2 * | 7/2003 | Bowe | 606/41 |
| 6,607,509 B2 | 8/2003 | Bobroff et al. | |
| 6,615,083 B2 | 9/2003 | Kupper | |
| 6,622,046 B2 | 9/2003 | Fraley et al. | |
| 2002/0016622 A1 | 2/2002 | Heil et al. | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082658 A1 | 6/2002 | Heinrich et al. | |
| 2002/0091414 A1 | 7/2002 | Bardy et al. | |
| 2002/0095184 A1 | 7/2002 | Bardy et al. | |
| 2002/0103510 A1 | 8/2002 | Bardy et al. | |
| 2002/0107544 A1 | 8/2002 | Ostroff et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0111663 A1 * | 8/2002 | Dahl et al. | 607/122 |
| 2002/0120299 A1 | 8/2002 | Ostroff et al. | |
| 2003/0004546 A1 | 1/2003 | Casey | |
| 2003/0004552 A1 | 1/2003 | Plombon et al. | |
| 2003/0023175 A1 | 1/2003 | Arzbaecher et al. | |
| 2003/0036778 A1 | 2/2003 | Ostroff et al. | |
| 2003/0045904 A1 | 3/2003 | Bardy et al. | |
| 2003/0069609 A1 | 4/2003 | Thompson | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |
| 2003/0212436 A1 | 11/2003 | Brown | |

FOREIGN PATENT DOCUMENTS

| | | |
|---|---|---|
| EP | 0 941 695 A | 9/1999 |
| WO | WO 92/20402 | 11/1992 |
| WO | WO 96/04955 A | 2/1996 |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek, *Defibrillation Threshold (DFT) Model of a Fully Subcutaneous ICD System*, Europace Supplements, vol. 2, Jun. 2001 at column 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

\* cited by examiner

EXPANDABLE FIXATION ELEMENTS FOR SUBCUTANEOUS ELECTRODES

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to leads for subcutaneously implantable cardiac monitoring and/or stimulation devices, and, more particularly, to expandable fixation elements for subcutaneous electrodes.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for monitoring the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure. For these reasons, subcutaneous ICDs are being developed.

Current ICDs utilize subcutaneous electrodes that may be prone to migrate in the subcutaneous tissue layer due to, for example, gravity, patient mobility, or patient interaction (e.g., twiddler's syndrome). Such migration may be detrimental to the performance of a subcutaneous electrode system because monitoring, detection, and defibrillation efficacy is typically very sensitive to electrode position/orientation.

Existing subcutaneous leads have typically relied on redundancy to address the problem of subcutaneous electrode migration. For example, a subcutaneous array may include three long coil electrodes, even though all three coils are not necessary when properly placed. Because migration may occur, the three long fingers provide adequate coverage to maintain defibrillation efficacy.

There is a need for more precise electrode placement that solves the problem of subcutaneous electrode migration. There is a further need for a fixation approach for subcutaneous leads that provides for improved subcutaneous system performance, such as by providing more consistent defibrillation and/or pacing thresholds and potentially lowering such thresholds. The present invention fulfills these and other needs, and addresses deficiencies in known systems and techniques.

SUMMARY OF THE INVENTION

The present invention is directed to subcutaneous systems and leads that, in general, can be fixed in tissue after placement. Embodiments of the present invention are directed to subcutaneous leads that incorporate one or more expanding fixation elements. Further embodiments of the present invention are directed to methods of placement and methods of fixation of subcutaneously implantable leads.

An implantable lead in accordance with an embodiment of the present invention is directed to a lead body with a supported electrode. The electrode is configured for subcutaneous non-intrathoracic placement within a patient. An expanding fixation element is provided on the implantable lead and configured to secure one or both of the subcutaneous electrode and the lead body in subcutaneous non-intrathoracic tissue. A delivery apparatus comprising a sheath may be included that is configured to introduce the lead to a desired subcutaneous non-intrathoracic location within the patient.

Another embodiment of the present invention is directed to a method of lead delivery involving introducing a sheath into a subcutaneous non-intrathoracic body location of a patient, providing a lead comprising a lead body and an electrode, and advancing the lead through the sheath and to the subcutaneous non-intrathoracic body location. The method further involves fixing the lead to subcutaneous non-intrathoracic tissue using an expanding fixation element and thereafter removing the sheath from the patient. The method may also involve longitudinally splitting the sheath when retracting the sheath from the patient and enabling an expandable fixation element for engagement with subcutaneous non-intrathoracic tissue.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
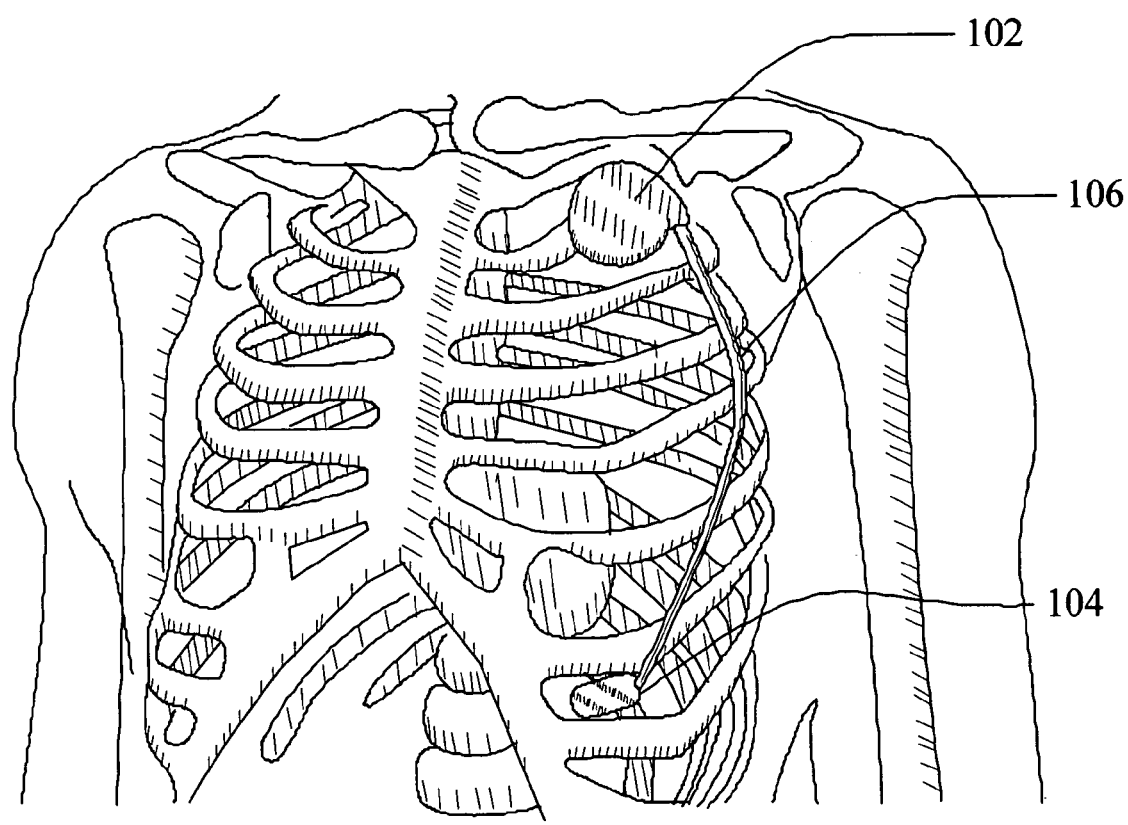
FIGS. 1A and 1B are views of a transthoracic cardiac monitoring and/or stimulation device as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

A device employing an implantable lead implemented in accordance with the present invention may incorporate one or more of the features, structures, methods, or combinations thereof described herein below. For example, a subcutaneous cardiac monitor or stimulator may be implemented to include one or more of the features and/or processes described below. It is intended that such a device or method need not include all of the features and functions described herein, but may be implemented to include selected features and functions that, in combination, provide for unique structures and/or functionality.

In general terms, an implantable lead implemented in accordance with the present invention may be used with a subcutaneous cardiac monitoring and/or stimulation device. One such device is an implantable transthoracic cardiac monitoring and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for monitoring cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Figure 1B:
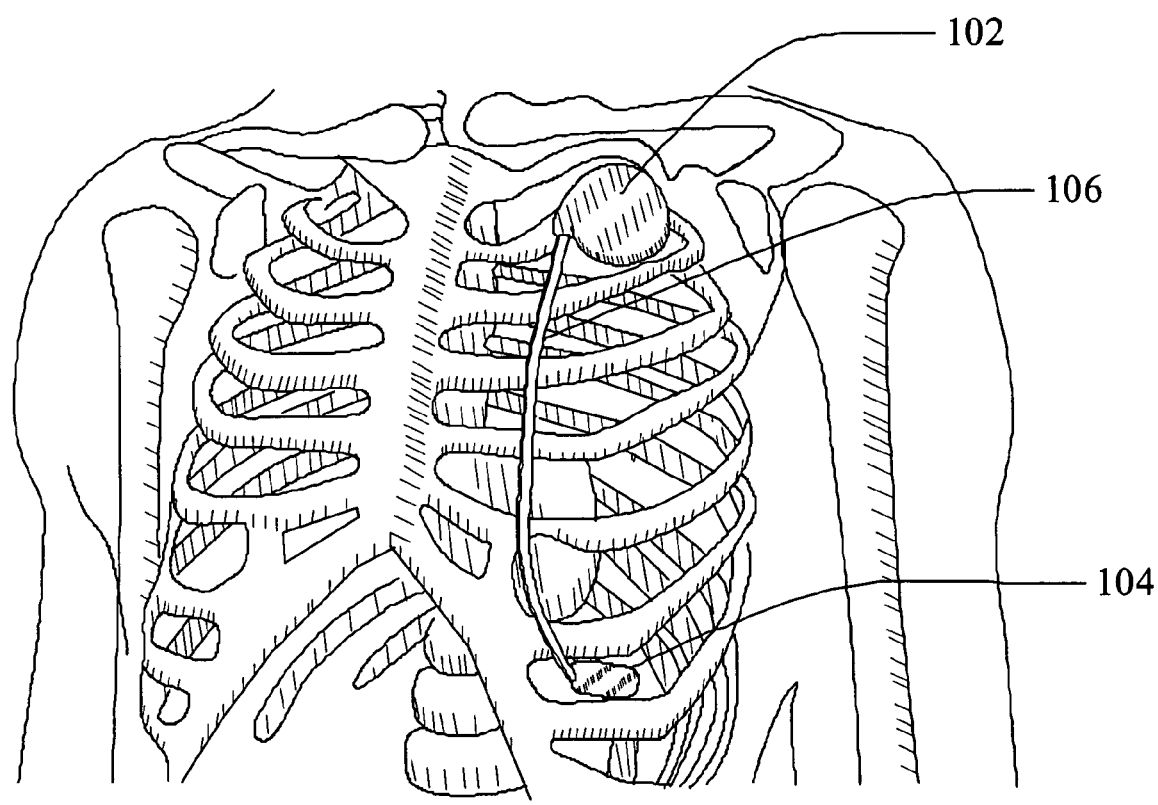

Referring now to FIGS. 1A and 1B of the drawings, there is shown a configuration of an ITCS device implanted in the chest region of a patient at different locations by use of a dissection tool. In the particular configuration shown in FIGS. 1A and 1B, the ITCS device includes a housing 102 within which various cardiac monitoring, detection, processing, and energy delivery circuitry may be housed. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed. An ITCS system according to this approach is distinct from conventional approaches in that it is preferably configured to include a combination of two or more electrode subsystems that are implanted subcutaneously.

In the configuration shown in FIGS. 1A and 1B, a subcutaneous electrode 104 may be positioned under the skin in the chest region and situated distal from the housing 102. The subcutaneous and, if applicable, housing electrode (s) may be positioned about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible. In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and the subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have, for example, an arcuate or angled shape.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly or both. Alternatively, a mechanical/electrical coupler may be used to establish mechanical and electrical connections between the rigid electrode support assembly and the housing 102. In such a configuration, a variety of different electrode support assemblies of varying shapes, sizes, and electrode configurations may be made available for physically and electrically connecting to a standard ITCS device.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst the subcutaneous electrodes 104. Accordingly, subcutaneous leads of the present invention may be shaped appropriately for specific electrodes or families of electrodes and electrode support assemblies.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, can incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 2:
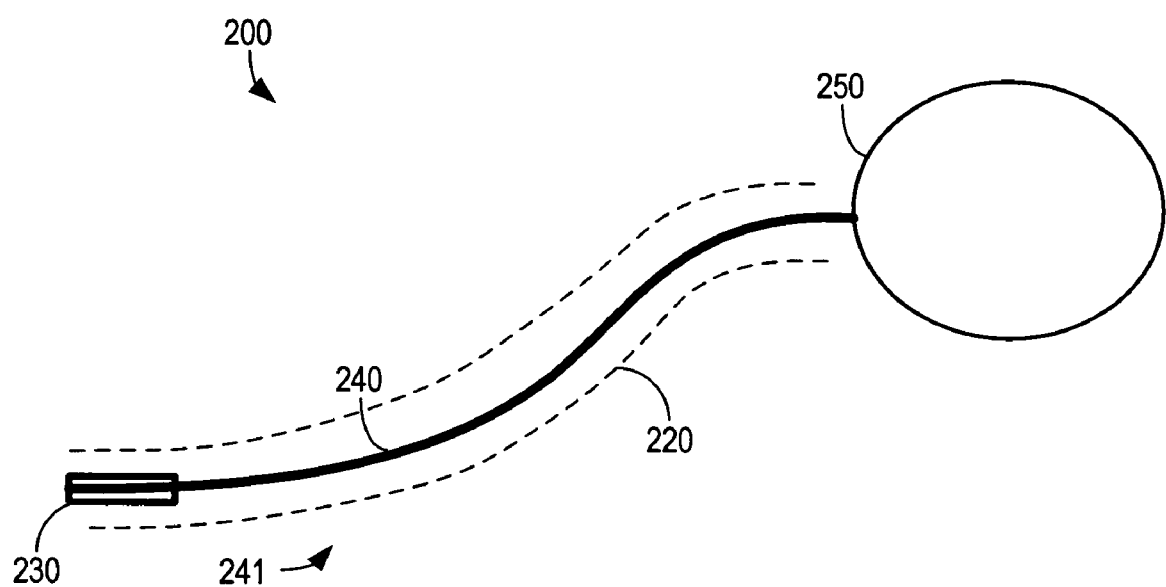
FIG. 2 illustrates a lead in accordance with the present invention, inserted in a dissected subcutaneous path leading from the can.

Referring now to FIG. 2, an ITCS system 200 is illustrated which includes a can 250 with a lead 241 inserted into a subcutaneous dissection path 220. The lead 241 includes an electrode 230 and a lead body 240. The electrode 230 is here illustrated at the distal end of the lead body 240. The subcutaneous dissection path 220 lies within subcutaneous tissue of a patient as illustrated in FIGS. 1A and 1B. The lead 241 may be inserted into the subcutaneous dissection path 220 by itself, or may also be inserted with use of a sheath 320 as illustrated in FIG. 3A.

Figure 3A:
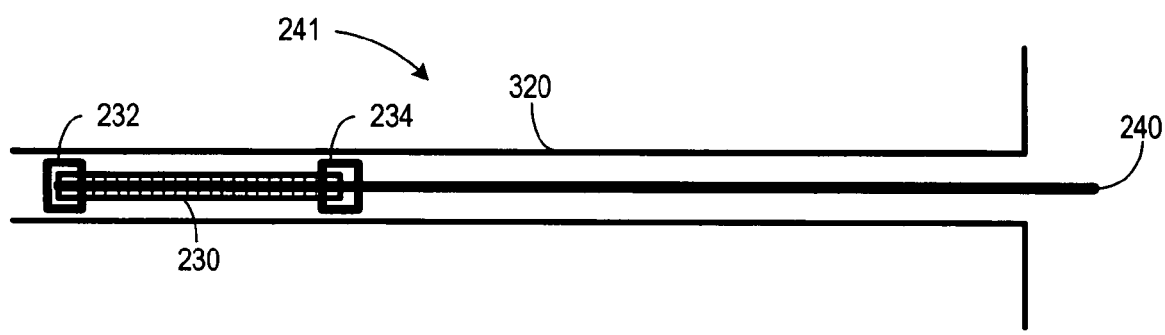
FIG. 3A is a plan view of a lead enclosed within a sheath prior to deployment of fixation elements in accordance with the present invention.

In FIG. 3A, a proximal end of the lead body 240 extends from the sheath 320, with the electrode 230 enclosed within the lumen of the sheath 320. The electrode 230 is illustrated that includes fixation elements 232 and 234 respectively provided at distal and proximal ends of the electrode 230. It should be understood that any number of such fixation elements may be employed to fix the electrode 230 within subcutaneous tissue.

The fixation elements 232 and 234 may include, for example, an expandable fixation mechanism, such as a spongy material that is preferably, but not necessarily, compressed within the lumen of the sheath 320 during delivery. According to one delivery approach, the lead 241 may be inserted into the dissection path, such as dissection path 220 shown in FIG. 2, while inside the sheath 320. After positioning the sheath 320 at the desired location within subcutaneous tissue, the sheath 320 may be retracted or otherwise separated from the lead 241. Retracting the sheath 320 from the electrode 230 and the lead body 240 permits the fixation elements 232 and 234 to expand and affix the electrode 230 within the subcutaneous tissue.

A suitable material for constructing the fixation elements 232 and 234 is scleral sponge. However, the fixation elements 232 and 234 may be constructed from any implantable material capable of expansion. Expansion of the fixation elements 232 and 234 may occur due to their release from the sheath 320, from uptake of body fluid, from an injected material, or other means of expansion. For example, a fluid may be injected into an expandable balloon fixation element with a one-way valve or stopper.

Figure 3B:
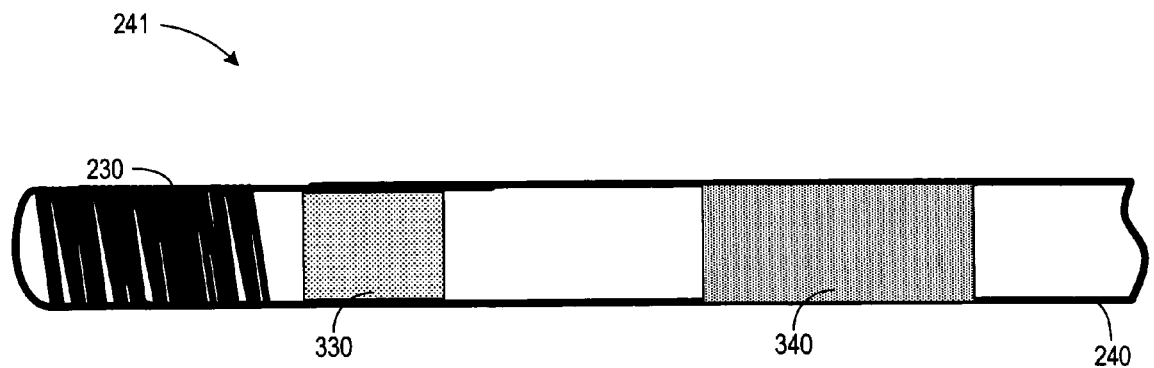
FIGS. 3B and 3C are plan views of a lead having an expanding region before (FIG. 3B) and after (FIG. 3C) expansion in accordance with the present invention.
Figure 3C:
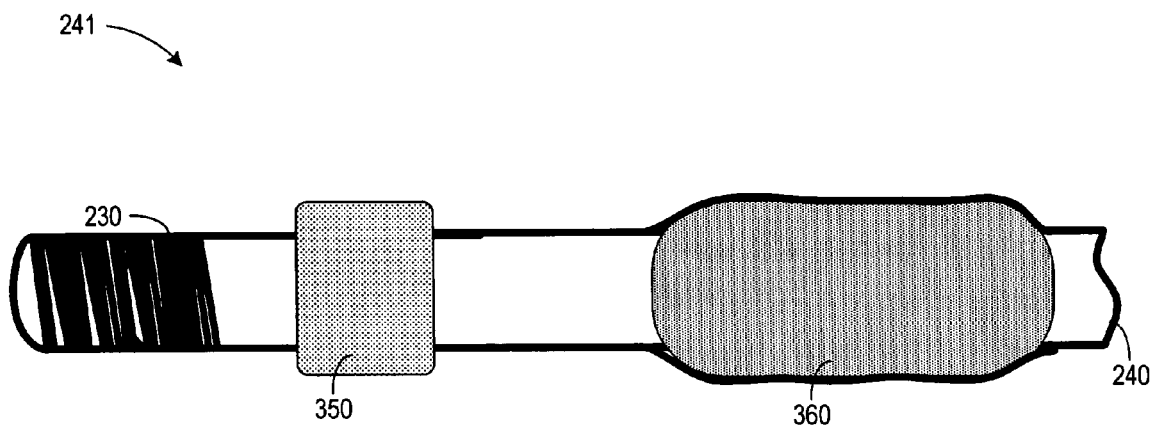

Other embodiments of expanding fixation elements are illustrated in FIGS. 3B and 3C. In FIG. 3B, an expanding collar 330 and an expanding lead portion 340 are illustrated in their respective pre-expansion configurations. The expanding collar 330 and lead portion 340 may, for example, be components made of a mixture of a biocompatible polymer and a water-soluble additive. By way of illustration, silicone rubber and a water-soluble additive such as glycerol represent one combination of materials useful for producing the expanding collar 330 and the expanding lead portion 340.

For example, the expanding collar 330 and/or lead portion 340 may include more than one additive and/or concentrations of one or more additives. At a first additive concentration, by way of illustration, the expanding collar 330 and/or lead portion 340 may expand for acute fixation, and remain expanded for continued chronic fixation. At a second additive concentration, by way of further illustration, the expanding collar 330 and/or lead portion 340 may expand for acute fixation, and the additive may then subsequently dissolve to provide pores that promote chronic tissue ingrowth. Similarly, a first additive may provide expansion and a second additive may provide porosity after the second additive is dissolved.

The expanded tip or collar 330 may itself provide a press-fit in the surrounding subcutaneous tissue, ensuring fixation, or may also provide porosity for promoting tissue ingrowth. By using other compositions, the additive(s) within the material may create pockets that combine within the component sufficiently to create pores that communicate with the component surface, which promotes tissue ingrowth. An example of additives that require a containment matrix or scaffolding for support include, but are not limited to, water soluble materials such as glycerol, mannitol, sodium chloride, and potassium chloride, as well as water soluble pharmaceutical agents such as, for example, dexamethasone sodium phosphate.

In another example involving use of expanding material compositions, an expanding polymer may be used alone or in combination with non-expanding polymers or other expanding materials. For example, a hydrogel may be used as an expanding polymeric additive to a non-expanding silicone, or in combination with an expanding material such as glycerol as is described above. A non-exhaustive, non limiting list of hydrogels useful in accordance with the present invention includes methyl methacrylate, poly(2-hydroxyethel methacrylate) gel, methacrylic acid, and other polyacid gels and methacrylate hydrogels.

Provision of an expanding polymer within or on an implantable lead body or lead component may provide for one or more of acute expanding fixation only, acute and chronic expanding fixation, and acute expanding fixation with dissolution of a non-polymeric additive for promoting tissue ingrowth and subsequent chronic fixation. A non-exhaustive non-limiting listing of expandable polymers useful in accordance with the present invention includes: vinylpyrrolidone, silicone rubber, polyurethane, polyacrylamide, and polyvinylpyrrolidone.

Polymeric expansion can be achieved in at least three ways. By way of a first example, a polymer may absorb environmental water in one of two fashions. Polymers that expand according to the first fashion are compounded with one or more of the additives listed above. The isolated additive inclusions will dissolve as water penetrates the polymer. Since the concentration of water in the isolated additive inclusion site would be less than that of the outer environment, water would naturally continue to enter the inclusion site, thereby bringing about expansion. This process would terminate once the growing internal "bubble" of additive solution encountered sufficient internal polymeric forces. In the event that the strength of the polymer was insufficient to generate those counteracting forces, the bubble would continue to grow until the bubble burst and the additive solution was released to the environment. This process would take place with any of the polymers listed.

Polymers that expand according to the second fashion absorb environmental water, and are usually provided initially in a dry state. Water or fluid absorption causes the polymeric component to expand. This is one mechanism for the hydrogel polymers list above. In the case of osmotic swelling utilizing an expanding polymer the absorbed water supplied by the body's aqueous environment penetrates the polymer to provide component expansion. The subsequent reaction forces generated within the material eventually balance the osmotic forces so that destructive expansion does not occur.

A second way expansion can be achieved uses a polymer that is exposed to changes in environmental pH. This is the case for some of the hydrogel formulations listed above. For example, a polymer such as the poly(2-hydroxyethel methacrylate) gel described above exhibits polymorphism of the polymer chain structure as pH changes. In a first state, the polymer may have a first structure that undergoes a change when it is immersed into the body's aqueous environment. The environmental pH will cause the polymer to change to a second structure, and bring about an expansion of the material. Further, the pH-sensitive polymers may also experience still further expansion when formulated with one or more additives listed above.

A third way expansion can be achieved uses a polymer that is exposed to an environment containing mobile substances, other than water, that would leave that environment to enter or partition into the polymer. A well-known example of this type of expansion is the uptake of lipid-like substances from the blood by early silicone rubber formulations such as materials used to manufacture early artificial heart valve poppets. Over time, after implantation, these silicone rubber poppets "soaked up" enough lipid-like substances to change the shape of the poppet and, in some cases, cause undesired valve failure. Modern formulations of silicone rubber are now available that do not exhibit this lipid-uptake behavior. However, the early formulations of silicone rubber may be beneficial for applications such as in the present invention. The absorption of lipid-like substances into a polymer, such as early formulation silicone, would bring about desired expansion to achieve fixation. Further, this expansion would be based upon a polymeric formulation, and not need the inclusion of additives to provide fixation.

In general, expandable polymer materials change shape in response to changes in their environment. Expanding polymers may be used by themselves, solely providing expansion, or may be used in combination with non-polymeric additives and/or other non-expanding polymers.

FIG. 3C illustrates an expanded collar 350 and an expanded lead portion 360. After implantation, collar 330 and lead portion 340 (shown in FIG. 3B) expand, and transform into expanded collar 350 and expanded lead portion 360. The expanded collar 350 and portion 360 may be employed in combination and/or by themselves, to fix the lead 241 into tissue.

Figure 4:
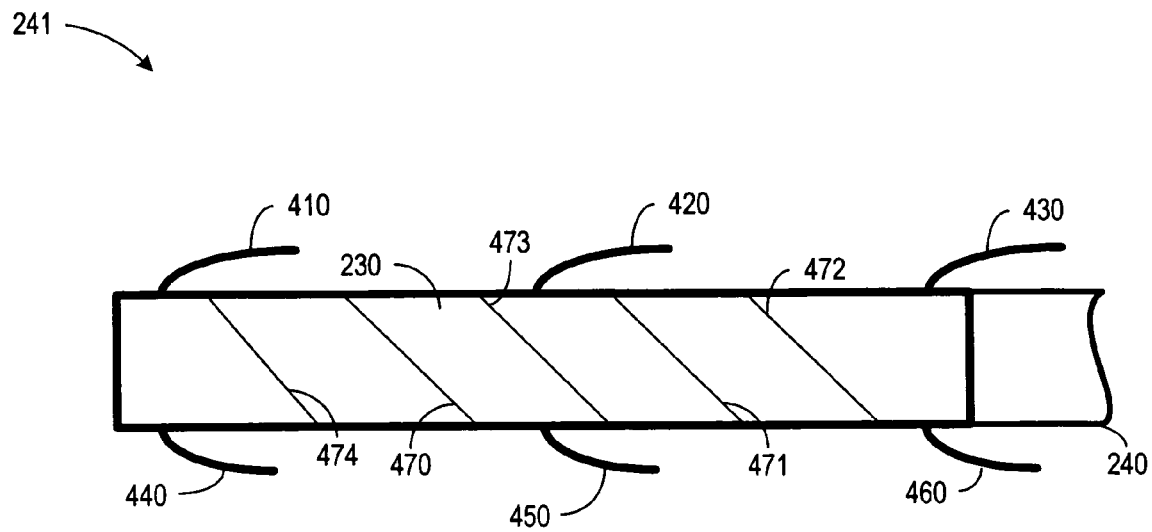
FIG. 4 is a magnified view of one embodiment of a lead having an electrode, the lead implemented to include fixation arrangements in accordance with the present invention.

Turning now to FIG. 4, there is illustrated an embodiment of the lead 241 that includes an electrode 230 provided with another fixation arrangement. The lead 241 is shown to include the electrode 230 now having tines 410, 420, 430, 440, 450, and 460 projecting outwardly from the body of the electrode 230/lead body 240. Also illustrated are a number of diagonal grooves 470, 471, 472, 473, and 474.

The tines 410-460 are shown biased away from the lead body 240 by, for example, manufacturing the times 410-460 using a mechanically elastic material having spring-like qualities such as, for example, metal or plastic. The tines 410-460 may be angled away and proximally oriented, as illustrated in FIG. 4, to allow the lead 241 to be easily inserted into the dissection path in a distal direction, but resist being pulled out in a proximal direction. The tines 410-460 provide for both acute and chronic fixation of the lead 241 into subcutaneous tissue.

Figure 5:
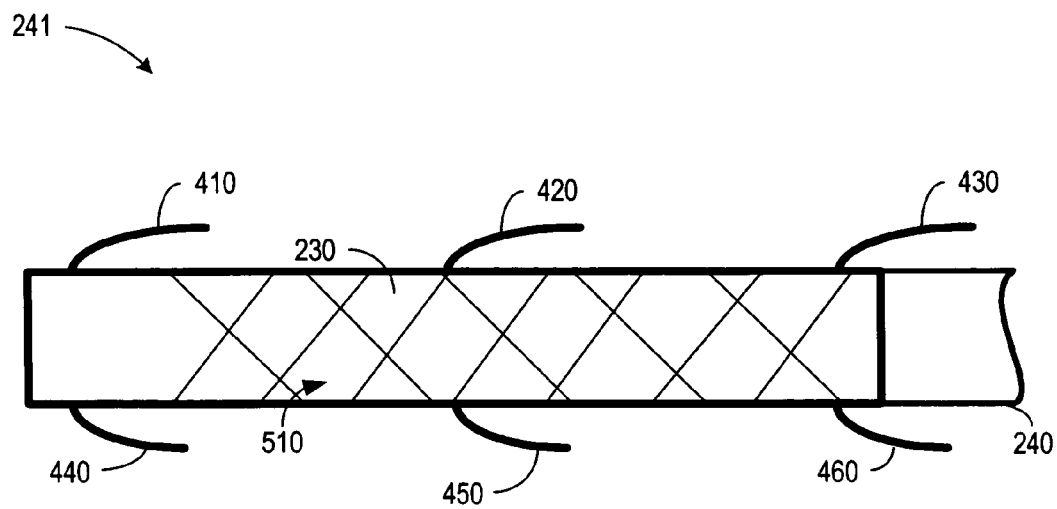
FIG. 5 is a magnified view of another embodiment of a lead having an electrode, the lead implemented to include fixation arrangements in accordance with the present invention.

After placement and acute fixation of the lead 241 within subcutaneous tissue, the grooves 470-474 provide regions for promoting tissue ingrowth, which chronically fixes the lead 241 within the subcutaneous tissue. The grooves 470-474 are denoted by a series of parallel lines oriented diagonally relative to a longitudinal axis of the lead body 240. It is contemplated that any number of grooves may be implemented at any angle or at varying angles. For example, a crosshatched pattern of grooves 510, as is illustrated in FIG. 5, may be incorporated to promote tissue ingrowth after placement of the lead 241 within subcutaneous tissue. The grooves 470-474 may be of any suitable size, shape, depth or spacing.

Figure 6:
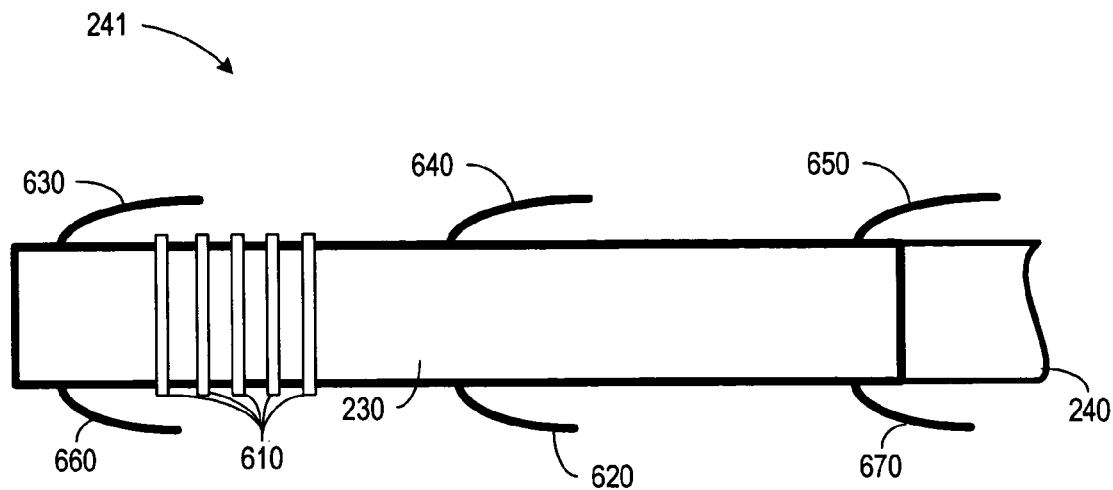
FIG. 6 is a magnified view of a further embodiment of a lead having an electrode, the lead implemented to include fixation arrangements in accordance with the present invention.

As illustrated in FIG. 6, one or more ridges 610 may be used in combination with, or in lieu of, grooves for chronic tissue purchase. The ridges 610 may be configured to provide for chronic fixation of the lead body 240 resulting from tissue ingrowth. Both grooves 510 (FIG. 5) and ridges 610 may also provide a degree of acute fixation, depending on the size of the grooves 510 or ridges 610. Acutely, the grooves 510 or ridges 610 would provide an initial purchase with the tissue. As time progresses, the initial immature encapsulation will constrict, resulting in a more firm purchase on the lead 241. As is further illustrated in FIG. 6, a plurality of tines 620, 630, 640, 650, 660, and 670 may be used in combination with other fixation techniques for purposes of acutely fixing the lead body 240 and/or a lead electrode, as described earlier. Features such as the plurality of tines 620, 630, 640, 650, 660, and 670 may be located on the lead body 240 and/or the electrode 230. The tines 620-670 and/or the ridges 610 and/or grooves may be used in various combinations along with other acute fixation techniques known in the art, such as, for example, a suture attachment point (not shown) on the lead 241.

Figure 7:
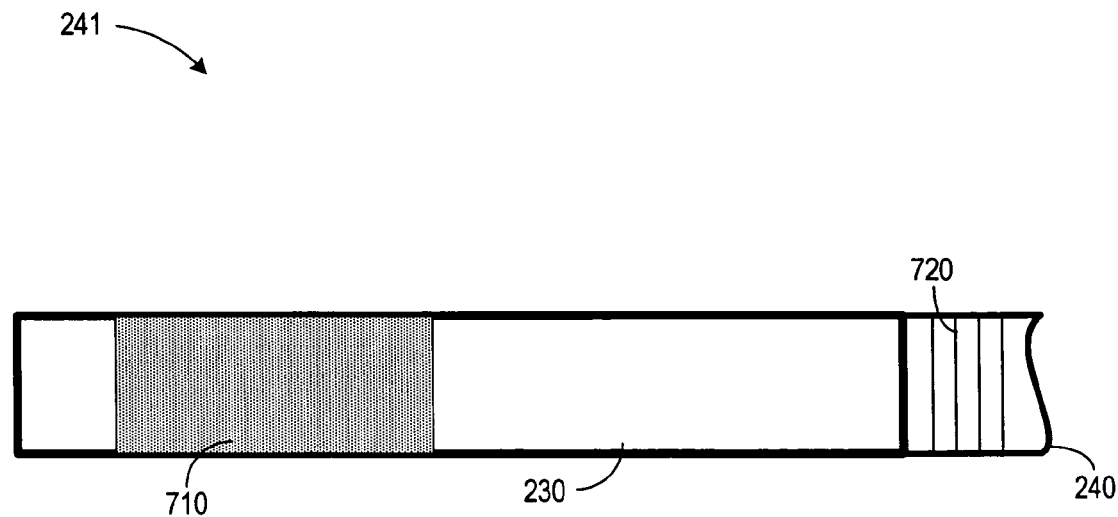
FIG. 7 is a magnified view of yet another embodiment of a lead having an electrode, the lead implemented to include fixation arrangements in accordance with the present invention.

Referring now to FIG. 7, another fixation arrangement in accordance with the present invention is illustrated. According to this embodiment, the fixation arrangement includes one or more textured surfaces or regions 710 on the lead body 240 and/or an electrode 230 of the lead 241. The textured surface(s) 710 may be employed as a sole chronic fixation method or in combination with other chronic fixation arrangements, such as a set of grooves 720 as is depicted in FIG. 7.

The textured surface 710 promotes tissue ingrowth to provide for chronic fixation of the lead body 240 into subcutaneous tissue. The textured surface 710 may be, for example, a porous region of the lead body 240, a coating having surface irregularities, dimples molded into the lead body 240 and/or a lead electrode 230, surface treatments from manufacturing processes such as sanding or scratching, or other suitable texturing.

Generally at least one acute fixation mechanism is employed in combination with chronic fixation mechanism, to allow sufficient time for the fixing of the chronic fixation mechanism into the subcutaneous tissue. An appropriate acute fixation mechanism is, for example, a suture placed at the distal end of the lead 241.

According to other fixation arrangements similar to those described above, and with reference to FIG. 7, the lead body 240 and/or the electrode 230 may be configured to incorporate tissue adhesion sites that facilitate chronic fixation of the lead body 240 and/or electrode 230 in subcutaneous tissue. For example, the adhesion sites may include voids in the sleeve of the lead body 240 at one or more locations of the sleeve. The adhesion sites may include exposed portions of one or more electrodes 230 or other exposed portions of the lead 241 insulation or covering.

According to another configuration, the adhesion sites may include a structure having a porous surface that promotes subcutaneous tissue in-growth or attachment at the adhesion sites. For example, a metallic annular structure may be disposed at the adhesion site. A metallic ring, for example, having porous surface characteristics may be employed to promote cellular adhesion at the adhesion site. The annular structure may incorporate the electrode 230 or be separate from the electrode 230.

In accordance with a further configuration, the adhesion sites may include a material that promotes subcutaneous tissue in-growth or attachment at the adhesion sites. For example, the bulk outer sleeve of the lead body 240 may be constructed that includes a first polymer material that substantially prevents tissue in-growth. Selective portions of the lead body 240 may include adhesion sites formed using a second polymer material that promotes tissue in-growth or attachment between the adhesion sites and subcutaneous tissue contacting the adhesion sites. The second polymer material may, for example, have a porosity, pore sizes or distribution of pore sizes that differ from that of the first polymer material. By way of further example, the second polymer material may differ in terms of hydrophobicity relative to the first polymer material.

In one particular configuration, the first polymer material may include a first type of PTFE (polytetrafluoroethylene), and the second polymer material of the adhesion sites may include a second type of PTFE. In one particular arrangement, the first type of PTFE includes a first type of ePTFE (expanded polytetrafluoroethylene), and the second type of PTFE includes a second type of ePTFE. The second type of ePTFE preferably differs from the first type of ePTFE in terms of one or more of porosity, pore sizes or distribution of pore sizes. Additional details of fixation approaches involving surface texturing, selective material use, and other arrangements that facilitate lead/electrode fixation via tissue ingrowth are disclosed in commonly owned U.S. patent application Ser. No. 10/004,708 (GUID.031 US01) filed Dec. 4, 2001 and entitled "Apparatus and Method for Stabilizing an Implantable Lead," which is hereby incorporated herein by reference.

Figure 8A:
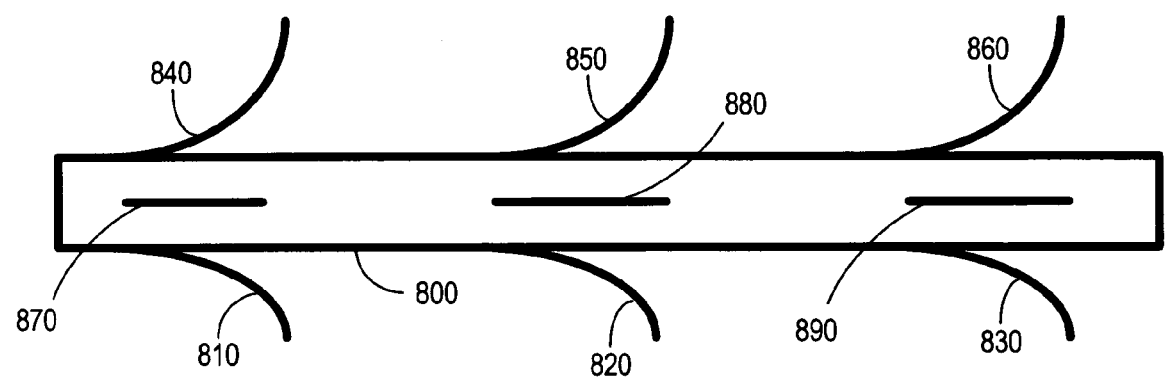
FIG. 8A is a magnified view of a further embodiment of a lead having an electrode, the lead implemented to include fixation arrangements in accordance with the present invention.
Figure 8B:
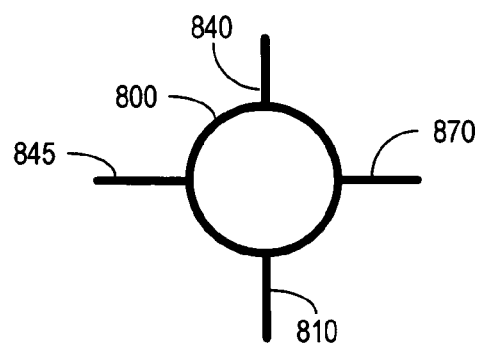
FIG. 8B is an end view of the embodiment illustrated in FIG. 8A.

Now referring to FIGS. 8A and 8B, details of acute fixation elements according to another embodiment of the present invention are shown. A lead 800 is illustrated that includes a plurality of tines 810, 820, 830, 840, 845 (FIG. 8B), 850, 860, 870, 880, and 890 (FIG. 8A). The tines 810-890 are shown disposed regularly with 90 degree circumferential placement, and regularly spaced along the length of the lead 800. However, other angles, regularity or irregularity, or number of tines may be employed in accordance with this embodiment. The tines 810-890 are shown, in this illustrative example, to be curved as they extend from the body of the lead 800. Curvature may assist in facilitating acute fixation by providing ease of movement of the lead 800 in a first direction (e.g., axial displacement in a distal direction), while helping to set the tines into tissue in response to movement in a second direction (e.g., axial displacement in a proximal direction). It is contemplated that the tines may be straight, or have a curvature tending away from or toward the body of the lead 800.

Figure 9A:
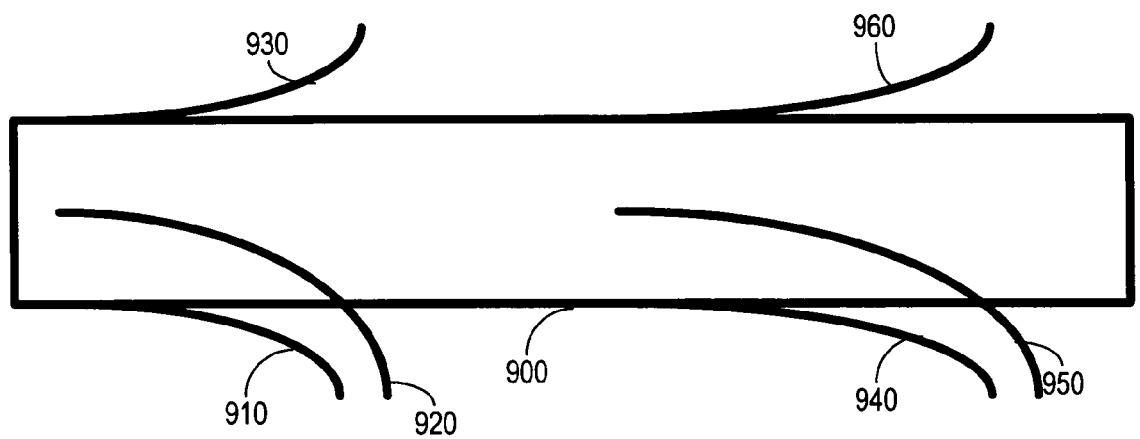
FIG. 9A is a magnified view of another embodiment of a lead having an electrode, the lead implemented to include a fixation arrangement in accordance with the present invention.
Figure 9B:
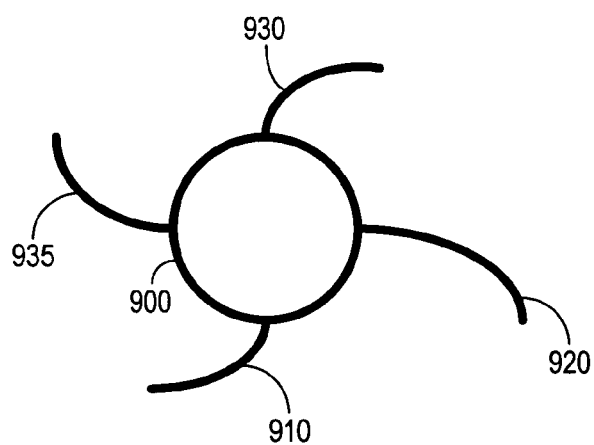
FIG. 9B is an end view of the embodiment illustrated in FIG. 9A.

Tines configured in accordance with the present invention may also be curved in more than one plane, as is illustrated in FIGS. 9A and 9B. A lead 900 (lead and/or electrode) is shown that includes tines 910, 920, 930, 935 (FIG. 9B), 940, 950, and 960 (FIG. 9A). As shown, the tines 910-960 are curved upward and away from the lead 900 relative to a longitudinal axis of the lead 900. The tines 910-960 are also curved around the circumference of the body of the lead 900 with respect to a second plane of reference.

The complex curvature illustrated in FIGS. 9A and 9B may be advantageous for optimally placing and fixing the lead 900 within subcutaneous tissue. This complex curvature provides for ease of inserting and withdrawing of the lead 900 when the lead 900 is rotated in a first direction. If the lead 900 is not rotated, the tines 910-960 set into the tissue. Further, if the lead 900 is rotated in the counter direction, the tines 910-960 may be forced into subcutaneous tissue.

Figure 9C:
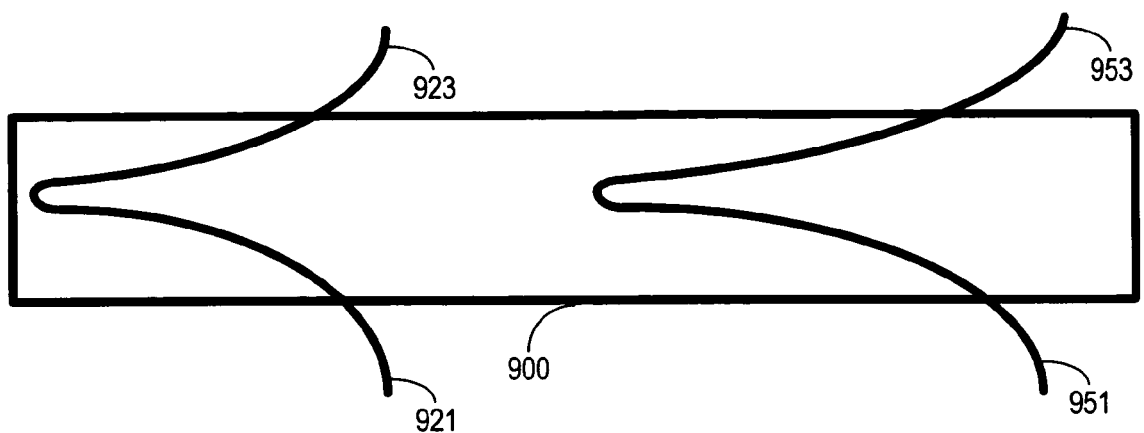
FIG. 9C is a magnified view of another embodiment of a lead having an electrode, the lead implemented to include a fixation arrangement in accordance with the present invention.
Figure 9D:
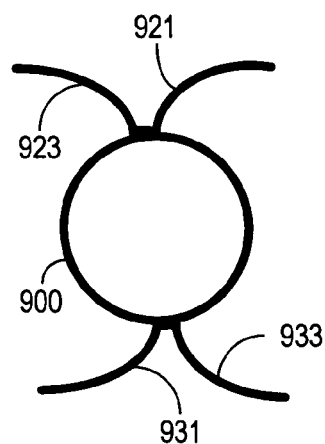
FIG. 9D is an end view of the embodiment illustrated in FIG. 9C.

Another tine configuration that employs complex curvature is illustrated in FIGS. 9C and 9D for optimally placing and fixing the lead 900 within subcutaneous tissue. This complex curvature provides for fixation from proximal displacement, and from rotation of the lead 900. Tines 921, 923, 931, 933, 951, and 953 set into the tissue due to their spring bias outwardly and upwardly from the lead 900. Placement of this type of lead fixation may be accomplished by direct distal insertion, to compress the tines 921, 923, 931, 933, 951, and 953 during placement and upon release of distal motion, the tines 921, 923, 931, 933, 951, and 953 spring outwardly from the lead 900 for fixation.

Figure 9E:
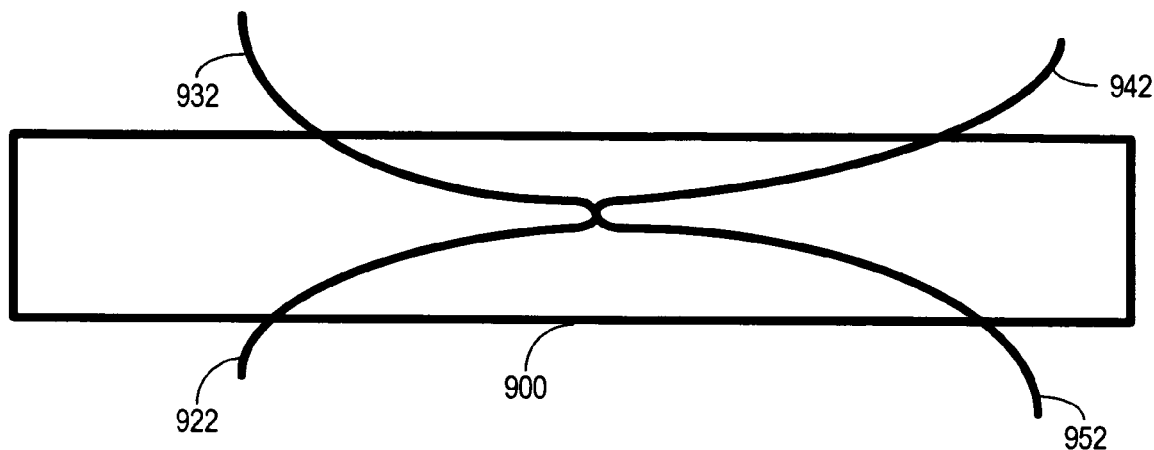
FIG. 9E is a magnified view of another embodiment of a lead having an electrode, the lead implemented to include a fixation arrangement in accordance with the present invention.
Figure 9F:
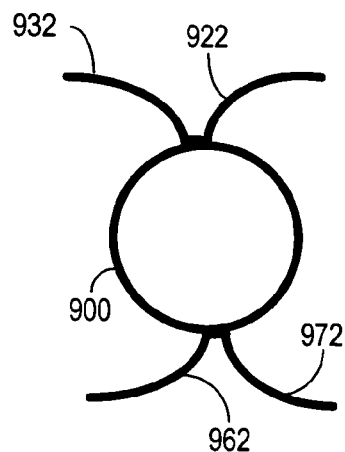
FIG. 9F is an end view of the embodiment illustrated in FIG. 9E.

A further tine configuration that employs complex curvature is illustrated in FIGS. 9E and 9F for optimally placing and fixing the lead 900 within subcutaneous tissue. This complex curvature provides for fixation from both proximal and distal displacement, and from rotation of the lead 900. Tines 922, 932, 942, 952, 962, and 972 set into the tissue due to their spring bias outwardly and upwardly from the lead 900. Placement of this type of lead fixation may be accomplished by utilization of a sheath, as described earlier, to compress the tines 922, 932, 942, 952, 962, and 972 during placement, and upon removal of the sheath, the tines 922, 932, 942, 952, 962, and 972 spring outwardly from the lead 900 for fixation.

Figure 9G:
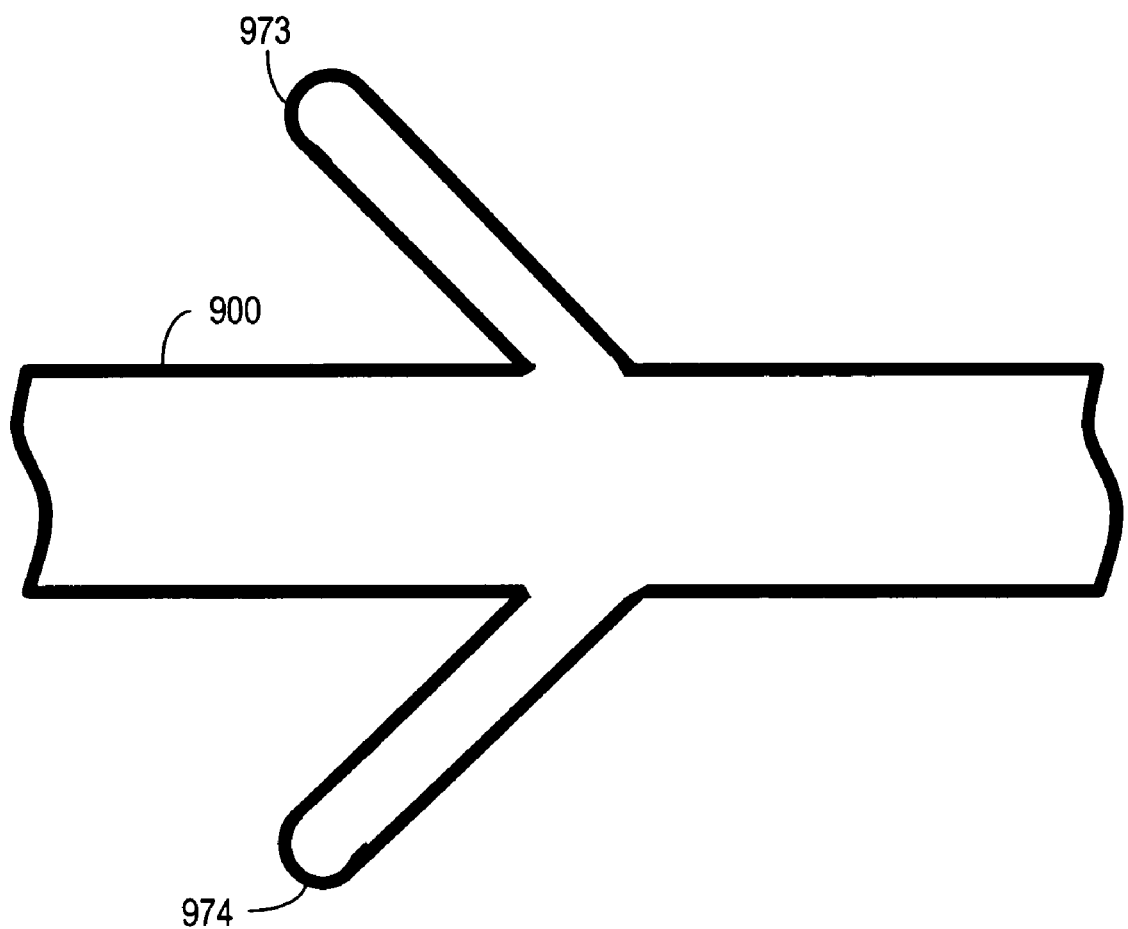
FIG. 9G is a magnified sectional view of another embodiment of a lead implemented to include a fixation arrangement in accordance with the present invention.

FIG. 9G is a magnified sectional view of another embodiment of a lead implemented to include a fixation arrangement in accordance with the present invention. Tines 973 and 974 set into the tissue due to their spring bias outwardly and upwardly from the lead 900. Placement of this type of lead fixation may be accomplished by utilization of a sheath, as described earlier, to compress the tines 973 and 974 during placement, and upon removal of the sheath, the tines 973 and 974 spring outwardly from the lead 900 for fixation.

Figure 10A:
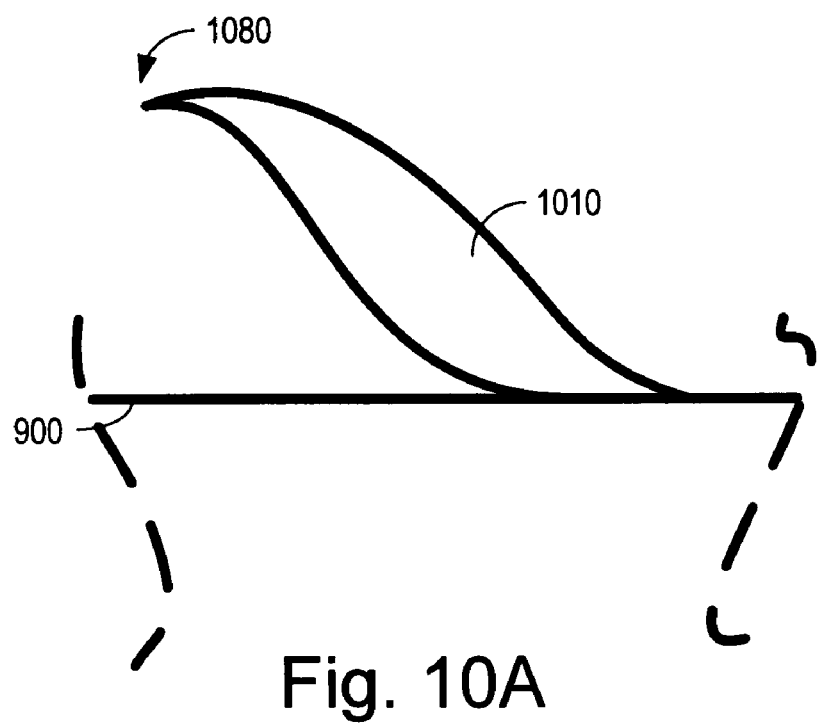
FIGS. 10A, 10B, 10C and. 10D are sectional views of various times in accordance with the present invention.

FIGS. 10A, 10B, 10C and 10D illustrate various shapes for tines in accordance with the present invention. In FIG. 10A, a tine 1010 is shown projecting from the lead 900. The tine 1010 has a single tip 1080. The tine 1010 is shaped to spring away from the lead 900 body.

For descriptive ease, consider a lead in the plane of FIGS. 10A, 10B, 10C and 10D, with the lead 900 moving from left to right in the plane of the figures. If the lead 900 were inserted, in this drawing from the left to the right, the tine 1010 would tend to collapse into the lead 900 and allow forward progress of the lead 900. If the lead 900 were to be pulled from right to left in FIG. 10A, the tine 1010 would tend to set into tissue by the single tip 1080.

Figure 10B:
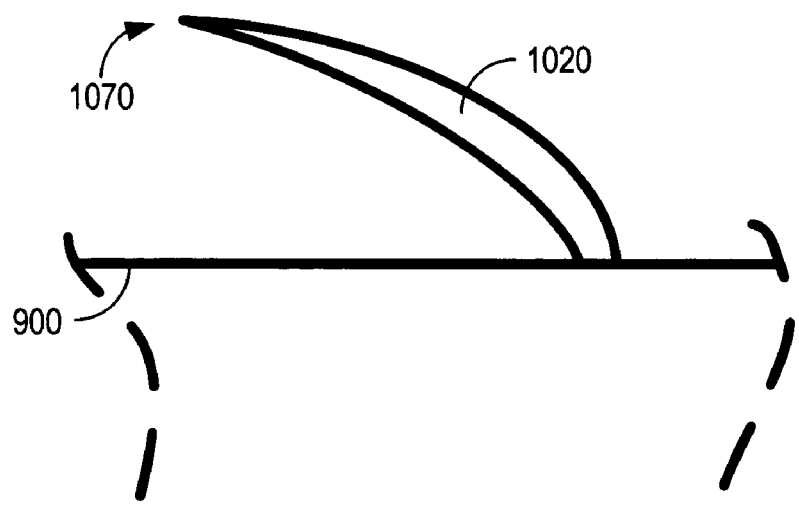

Similarly to the tine of FIG. 10A, a tine 1020 of FIG. 10B would also flex and set under the same movement. However, the tine 1020, not as substantial as the tine 1010 of FIG. 10A, would more easily collapse and compress under left to right motion, and may provide less resistance to right to left motion.

Figure 10C:
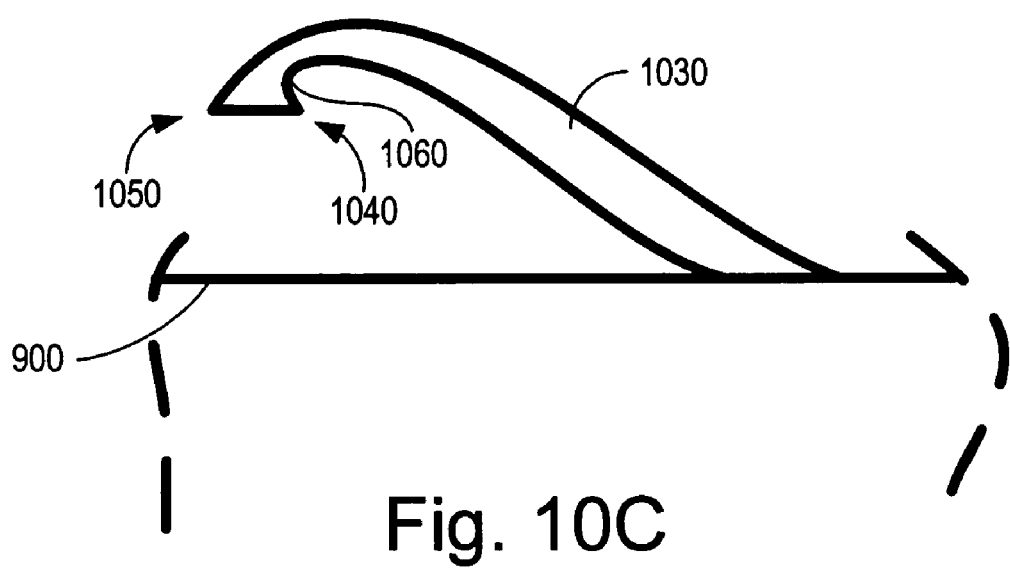

Referring now to FIG. 10C, a tine 1030 is illustrated with a first point 1050 and a second point 1040. The shape of the tine 1030, along with the second point 1040, creates a barb 1060. The barb 1060, similar to a fishhook barb, provides for not only resistance to right to left motion, but also for resistance to further left to right motion after being set. This arrangement provides for ease of insertion in a left to right direction, a resistance to right to left movement, and subsequently also provides resistance to further left to right movement after being set.

Figure 10D:
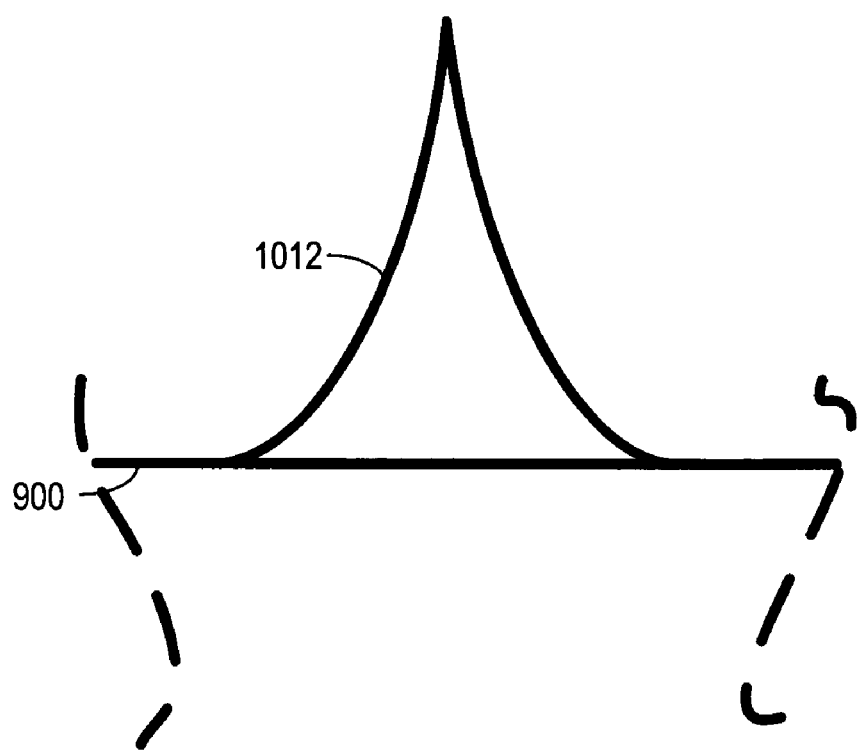

Referring to FIG. 10D, a straight tine 1012 is illustrated perpendicularly projecting from the lead 900 body. The straight tine 1012 may be compressed and/or spring biased in the lumen of a sheath (such as, for example, the sheath 320 in FIG. 3A) during delivery of the lead 900, such that the straight tine 1012 sets into tissue when the sheath is removed. In another embodiment, the rigidity of the straight tine 1012 may be designed such that a set level of resistance is provided by the straight tine 1012 when it is moved within tissue. By adjusting the rigidity, the level of fixation of the lead 900, and the associated ease of insertion/relocation, may be predetermined by design. Rigidity may be altered by material selection, geometry, of other means known in the art.

Figure 11:
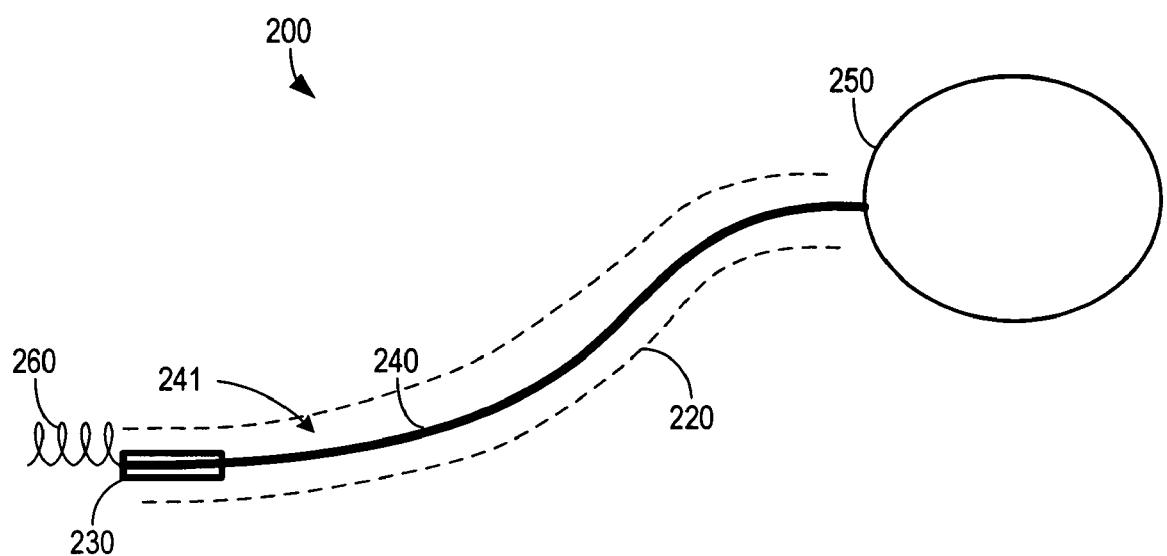
FIG. 11 illustrates a lead in accordance with the present invention, inserted in a dissected subcutaneous path leading from the can, where an offset helical electrode/fixation element is illustrated fixed to the tissue.

Referring now to FIG. 11, an ITCS system 200 is illustrated which includes a can 250 with a lead 241 inserted into a dissection path 220. The lead 241 includes an electrode 230, here illustrated at the distal end of the lead body 240. The subcutaneous dissection path 220 lies within subcutaneous tissue of a patient as illustrated in FIGS. 1A and 1B. An offset helix 260 is employed as a fixation element useable to fix the lead 241 into tissue in accordance with the present invention. Typically, the helix 260 is configured to define all or at least part of the electrode 230.

Figure 12:
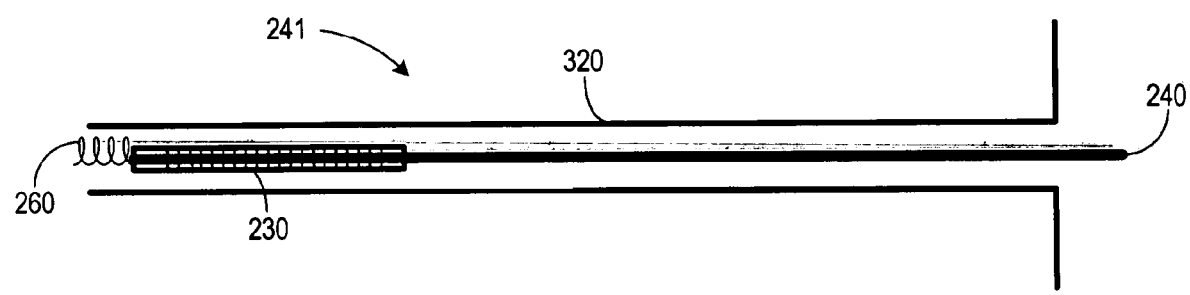
FIG. 12 is a plan view of a lead enclosed within a sheath prior to deployment of a fixation element in accordance with the present invention.

FIG. 12 illustrates the lead 241 inserted into the tear-away sheath 320 as described with an earlier embodiment. After placing the lead 241 in subcutaneous tissue, the sheath 320 is retracted from the subcutaneous tunnel, typically in a peel-away fashion. The lead 241 may be fixed into the tissue by rotating the lead 241 as will be described in further detail below.

Figure 13:
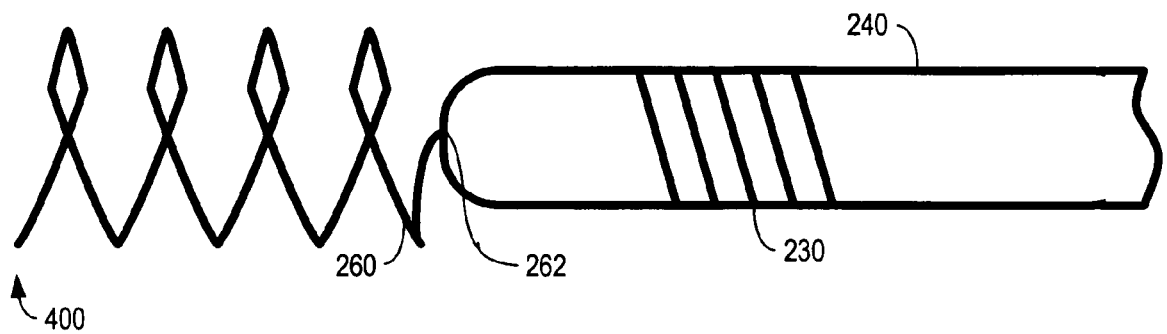
FIG. 13 is a magnified view of one embodiment of a lead having an electrode, the lead implemented to include a fixation arrangement in accordance with the present invention.
Figure 14:
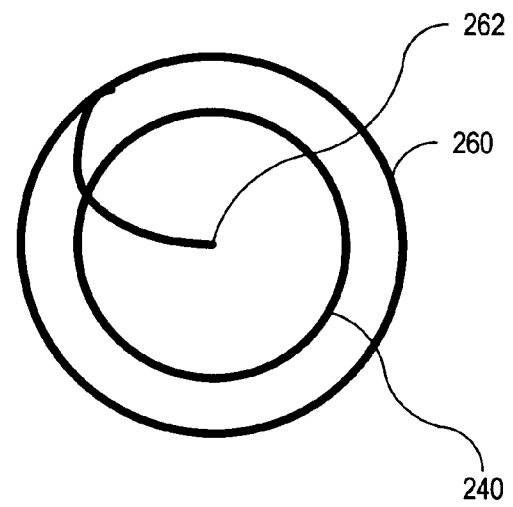
FIG. 14 is a magnified end view of the embodiment of FIG. 13.

FIGS. 13 and 14 show a plan view and end view respectively of an embodiment of the present invention. In FIG. 13, a helical coil 260 may be used as a fixation element to fix the lead body 240 into tissue when the electrode 230 is positioned in a desired location. The helical coil 260 is attached to the distal end of the lead body 240 at attachment point 262. Rotation of the lead body 240 causes rotation of the helical coil 260, thereby rotating sharp end 400.

Although helical coil 260 is illustrated having uniform pitch, cylindrical cross-section, constant thickness of coil, it is contemplated that any helical or screw-like structure may be used in accordance with the present invention. The helix may be of non-uniform and/or tapering cross-section; the pitch may be non-uniform; and the shape and thickness of the coil may be varied without departing from the scope of the present invention.

As the lead 241 is rotated, the sharp end 400 contacts the wall of the dissected tissue path and penetrates into subcutaneous tissue. As the lead 241 is further rotated, the sharp end 400 burrows through the tissue, repeatedly penetrating the wall and progressing forward as the winding of the helical coil 260 dictates. This effectively screws the helical coil 260 into the wall of the tissue, thus fixing the lead 241.

In another embodiment, the helical coil 260 may be rotatable independently of the lead 241. As the helical coil 260 is rotated or formed via extension, the sharp end 400 contacts the wall of the dissected tissue path and penetrates into subcutaneous tissue. As the helical coil is further rotated or further extended, the sharp end 400 burrows through the tissue, repeatedly penetrating the wall and progressing forward as the winding of the helical coil 260 dictates. This effectively screws the helical coil 260 into the wall of the tissue, thus fixing the lead 241.

In the embodiment illustrated in FIGS. 13 and 14, the helical coil 260 is seen to be larger in diameter than the lead body 240. An advantage of employing the helical coil 260 that is larger than the lead body 240 is the assurance that as the lead lies within the dissected tissue tunnel, the sharp end 400 penetrates the tunnel wall and provide fixation when rotated. If the helical coil 260 were the same size or smaller than the lead body 240 diameter, the lead body may prevent the sharp end 400 from initiating penetration unless the lead body 240 is pushed distally along the dissection tunnel until penetration occurs. This pushing of the lead may cause the electrode 230 to be moved distally from an optimum fixation location.

Figure 15:
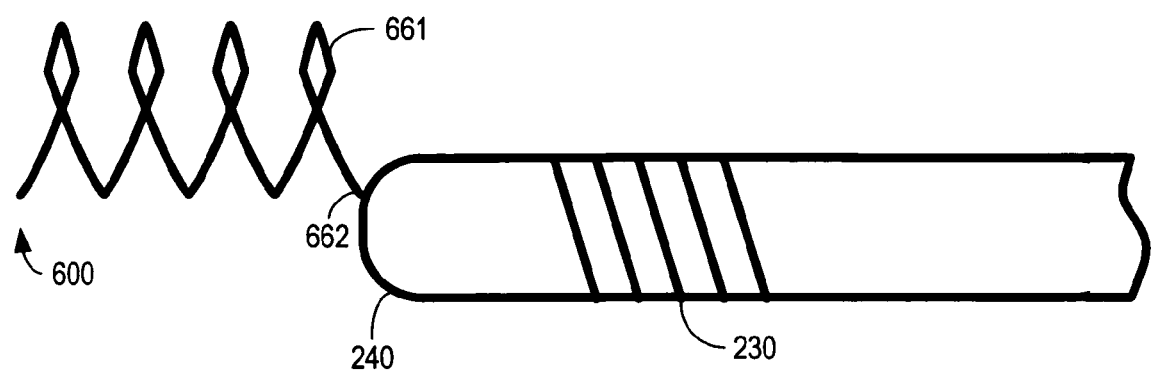
FIG. 15 is a magnified view of a further embodiment of a lead having an electrode, the lead implemented to include a fixation arrangement in accordance with the present invention.
Figure 16:
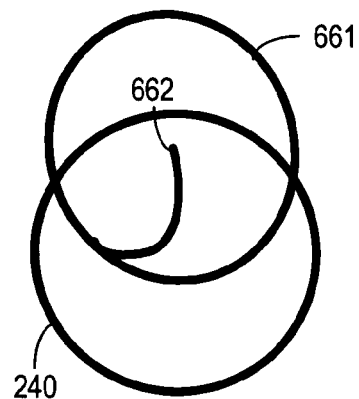
FIG. 16 is a magnified end view of the embodiment of FIG. 15.

Referring now to FIGS. 15 and 16, a plan view and end view respectively of another embodiment of the present invention is illustrated. In FIG. 15, an offset helical coil 661 may be used as a fixation element to fix the lead body 240 into tissue when the electrode 230 is positioned in a desired location. The offset helical coil 661 is attached to the distal end of the lead body 240 at attachment point 662. Rotation of the lead body 240 causes rotation of the offset helical coil 661, rotating sharp end 600.

As the lead body 240 is rotated, the sharp end 600 contacts the wall of the dissected tissue path and penetrates into subcutaneous tissue. As the lead body 240 is further rotated, the sharp end 600 burrows through the tissue, repeatedly penetrating the wall and progressing forward as the winding of the offset helical coil 661 dictates. This effectively screws the offset helical coil 661 into the wall of the tissue, thus fixing the lead 241.

In the embodiment illustrated in FIGS. 15 and 16, as best seen in FIG. 16, the offset helical coil 661 is seen to have an offset central axis relative to the longitudinal axis of the lead body 240. An advantage of employing the offset helical coil 661 offset from the lead body 240 is the assurance that as the lead lies within the dissected tissue tunnel, the sharp end 600 penetrates the tunnel wall and provides fixation when rotated.

Coils 260 and 661 may be manufactured using a spring material such as, for example, metal, such that coils 260 and 661 deform within the sheath 320 when being advanced to their fixation locations. Upon removal of the sheath 320, coils 260 and 661 spring into their larger or offset configurations to affect fixation into tissue. Coils 260 and 661 may also be manufactured using a shape memory alloy such as, for example, Nitinol, such that coils 260 and 661 have a first, non-penetrating shape, when being advanced through the dissection path. Upon being subjected to body temperature or artificially heated, coils 260 and 661 return to a shape such as described above to affect fixation.

It should be understood that any number, type, or combination of fixation elements have been contemplated, and that the number, types, and combinations presented above are by way of example only. Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable lead configured for placement within a tunnel formed in subcutaneous non-intrathoracic tissue, comprising:
    a lead body;
    a cardiac electrode supported by the lead body, the cardiac electrode configured for one or both of sensing cardiac activity and delivering cardiac stimulation energy from a location within the tunnel; and
    an expandable fixation element provided on the implantable lead and comprising a material that undergoes a volumetric change when placed in subcutaneous non-intrathoracic tissue, the expandable fixation element configured to expand by body fluid absorption and to chronically secure one or both of the cardiac electrode and the lead body within subcutaneous non-intrathoracic tissue defining the tunnel by tissue in-growth into pores of the expandable fixation element.

2. The lead according to claim 1, wherein the expandable fixation element is provided on the cardiac electrode.

3. The lead according to claim 1, wherein the expandable fixation element comprises a sponge.

4. The lead according to claim 1, wherein the expandable fixation element comprises a scleral sponge.

5. The lead according to claim 1, wherein the expandable fixation element comprises a plurality of sponges arranged in a spaced relationship.

6. The lead according to claim 1, wherein the expandable fixation element comprises an expandable portion of the lead body.

7. The lead according to claim 6, wherein the expandable portion of the lead body comprises an additive in a polymer.

8. The lead according to claim 7, wherein the additive comprises glycerol.

9. The lead according to claim 6, wherein the expandable portion of the lead body comprises an expandable polymer.

10. The lead according to claim 9, wherein the expandable polymer comprises hydrogel.

11. The lead according to claim 1, wherein the expandable fixation element comprises an expandable collar coupled to the lead body.

12. The lead according to claim 11, wherein the expandable collar comprises an additive in a polymer.

13. The lead according to claim 12, wherein the additive comprises glycerol.

14. An implantable lead system configured for placement within a tunnel formed in subcutaneous non-intrathoracic tissue, comprising:
   a lead comprising a lead body and a cardiac electrode, the lead configured for placement within the tunnel, the cardiac electrode configured for one or both of sensing cardiac activity and delivering cardiac stimulation energy from a location within the tunnel;
   an expandable fixation element provided on the lead and comprising a material that undergoes a volumetric change when placed in subcutaneous non-intrathoracic tissue, the expandable fixation element configured to expand by body fluid absorption and to chronically secure one or both of the cardiac electrode and the lead body within subcutaneous non-intrathoracic tissue defining the tunnel by tissue in-growth into pores of the expandable fixation element; and
   a delivery apparatus configured to introduce the lead to a desired subcutaneous non-intrathoracic location within the tunnel.

15. The lead system according to claim 14, wherein the expandable fixation element comprises one or more sponges.

16. The lead system according to claim 14, wherein the expandable fixation element comprises one or more scleral sponges.

17. The lead system according to claim 14, wherein a lumen of the delivery apparatus is dimensioned to compress the expandable fixation element while permitting axial displacement of the lead within the lumen.

18. The lead system according to claim 14, wherein the delivery apparatus comprises a sheath having a longitudinal pre-stress line arrangement to facilitate sheath separation during retraction of the sheath from the patient.

19. The lead system according to claim 14, wherein the expandable fixation element is provided on the cardiac electrode.

20. The lead system according to claim 14, wherein the expandable fixation element comprises a plurality of sponges arranged in a spaced relationship.

21. The lead system according to claim 14, wherein the expandable fixation element comprises an expandable portion of the lead body.

22. The lead system according to claim 21, wherein the expandable portion of the lead body comprises an additive in a polymer.

23. The lead system according to claim 22, wherein the additive comprises glycerol.

24. The lead according to claim 21, wherein the expandable portion of the lead body comprises an expandable polymer.

25. The lead system according to claim 24, wherein the expandable polymer comprises a hydrogel.

26. The lead system according to claim 14, wherein the expandable fixation element comprises an expandable collar coupled to the lead body.

27. The lead system according to claim 26, wherein the expandable collar comprises an additive in a polymer.

28. The lead system according to claim 27, wherein the additive comprises glycerol.

29. The lead according to claim 26, wherein the expandable collar comprises an expandable polymer.

30. The lead system according to claim 29, wherein the expandable polymer comprises a hydrogel.

31. A method of lead stabilization, comprising:
   creating a tunnel in subcutaneous non-intrathoracic tissue of a patient;
   providing a lead comprising a lead body, a cardiac electrode, and an expandable fixation element comprising a material that undergoes a volumetric change when placed in subcutaneous non-intrathoracic tissue, the cardiac electrode configured for one or both of sensing cardiac activity and delivering cardiac stimulation energy from a location within the tunnel;
   advancing the lead into the tunnel; and
   volumetrically expandably securing one or both of the lead body and the cardiac electrode within subcutaneous non-intrathoracic tissue defining the tunnel at a fixation site using the expandable fixation element.

32. The method according to claim 31, wherein the expandable fixation element expands to an effective diameter larger than the diameter of the lead body to engage the subcutaneous non-intrathoracic tissue at the fixation site.

33. The method according to claim 31, wherein the expandable fixation element comprises one or more expandable fixation elements that expand to fixedly engage the subcutaneous non-intrathoracic tissue at one or more fixation sites.

34. The method according to claim 31, further comprising modifying the position or orientation of the expandable fixation element when the lead is advanced within the lumen.

35. The method according to claim 34, wherein modifying the position or orientation comprises resiliently displacing the expandable fixation element when the lead is advanced within the lumen.

36. A method of lead delivery, comprising:
   creating a tunnel in subcutaneous non-intrathoracic tissue of a patient;
   introducing a sheath into the tunnel;
   providing a lead comprising a lead body and a cardiac electrode configured for one or both of sensing cardiac activity and delivering cardiac stimulation energy from a location within the tunnel, the lead comprising an expandable fixation element that undergoes a volumetric change when placed in subcutaneous non-intrathoracic tissue;
   advancing the lead through the sheath and into the tunnel;
   volumetrically expandably fixing the lead within subcutaneous non-intrathoracic tissue defining the tunnel by tissue in-growth into pores of the expandable fixation element; and
   removing the sheath from the patient.

37. The method according to claim 36, wherein removing the sheath comprises longitudinally splitting the sheath when removing the sheath from the patient.

38. The method according to claim 36, wherein removing the sheath comprises enabling the fixation element for expandably fixing the lead within the subcutaneous non-intrathoracic tissue.

39. The method according to claim 36, wherein advancing the lead through the sheath comprises modifying a position or an orientation of the expandable fixation element provided on one or both of the lead body and cardiac electrode.

40. The method according to claim 36, wherein advancing the lead through the sheath comprises compressing the expandable fixation element provided on one or both of the lead body and cardiac electrode.

41. The method according to claim 36, wherein fixing the lead comprises expanding a portion of the lead to fix one or both of the lead body and the electrode within the subcutaneous non-intrathoracic tissue.

42. An implantable lead configured for placement within a tunnel formed in subcutaneous non-intrathoracic tissue, comprising:
   a lead body;
   a cardiac electrode supported by the lead body, the cardiac electrode configured for one or both of sensing cardiac activity and delivering cardiac stimulation energy from a location within the tunnel; and
   a volumetrically expandable portion provided on the implantable lead, the expandable portion configured to expand by bodily fluid absorption and to provide pores that promote tissue in-growth for chronic fixation to subcutaneous non-intrathoracic tissue defining the tunnel.

43. The lead according to claim 42, wherein the expandable portion comprises an additive in a polymer.

44. The lead system according to claim 43, wherein the additive comprises glycerol.

45. The lead according to claim 42, wherein the expandable portion comprises an expandable polymer.

46. The lead system according to claim 45, wherein the expandable polymer comprises a hydrogel.

47. The lead system according to claim 42, wherein the expandable portion comprises one or more sponges.

48. The lead system according to claim 42, wherein the expandable portion comprises one or more scleral sponges.

49. The lead system according to claim 42, wherein the expandable portion comprises an expandable collar coupled to the implantable lead.

50. The lead according to claim 42, wherein the expandable portion comprises first and second additives, the first additive configured to provide expansion and the second additive configured to provide the pores.

51. The lead according to claim 42, wherein the expandable portion comprises a polymer having first and second additive concentrations, the first additive concentration configured to provide expansion and the second additive concentration configured to provide the pores.

* * * * *